US011819420B2

(12) United States Patent
Jang et al.

(10) Patent No.: US 11,819,420 B2
(45) Date of Patent: Nov. 21, 2023

(54) SPINAL INTERVERTEBRAL BODY FUSION DEVICE

(71) Applicant: INDUSTRIAL TECHNOLOGY RESEARCH INSTITUTE, Hsinchu (TW)

(72) Inventors: Fang-Jie Jang, Keelung (TW); Pei-I Tsai, Hsinchu (TW); Chih-Chieh Huang, Miaoli County (TW); De-Yau Lin, Tainan (TW); Wei-Lun Fan, Miaoli County (TW); Yi-Hung Wen, Hsinchu (TW); Kuo-Yi Yang, Hsinchu (TW); Hsin-Hsin Shen, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 681 days.

(21) Appl. No.: 16/725,481

(22) Filed: Dec. 23, 2019

(65) Prior Publication Data
US 2021/0137699 A1    May 13, 2021

(30) Foreign Application Priority Data
Nov. 8, 2019   (TW) .................................. 108140606

(51) Int. Cl.
*A61F 2/44*   (2006.01)
*A61F 2/30*   (2006.01)

(52) U.S. Cl.
CPC ........ *A61F 2/4455* (2013.01); *A61F 2/30724* (2013.01); *A61F 2002/30985* (2013.01)

(58) Field of Classification Search
CPC .. A61F 2002/30507; A61F 2002/30556; A61F 2002/30579; A61F 2/4425;
(Continued)

(56) References Cited

U.S. PATENT DOCUMENTS 5,522,899 A * 6/1996 Michelson .............. A61F 2/447
                                                                606/279
8,535,380 B2   9/2013 Greenhalgh et al.
(Continued)

FOREIGN PATENT DOCUMENTS

CN     102014801 B    2/2014
CN     103876865 B    4/2016
(Continued)

OTHER PUBLICATIONS

Kwan et al., "Automatic boundary extraction and rectification of bony tissue in CT images using artificial intelligence techniques" Jun. 2000.
(Continued)

*Primary Examiner* — Christopher D. Prone
(74) *Attorney, Agent, or Firm* — Maschoff Brennan

(57) ABSTRACT

The disclosure relates to a spinal intervertebral body fusion device including an adjustable spacer, a first and second pushing piece, and an operative piece. The adjustable spacer includes a first and second supporting plate. The first supporting plate portion is movably installed on the second supporting plate portion. The first and second supporting plate portions form a first and second opening respectively located at two opposite sides of the adjustable spacer. The first pushing piece located at the first opening and is partially clamped by the first and second supporting plate portions. The second pushing piece located at the second opening is partially clamped by the first and second supporting plate portions. The operative piece is movably disposed through the second pushing piece and screwed to the first pushing piece. The operative piece has an annular slot, and the second pushing piece is partially located in the annular slot.

15 Claims, 14 Drawing Sheets

(58) Field of Classification Search
CPC ............... A61F 2/447; A61F 2002/443; A61F 2002/30985; A61F 2/30724; A61F 2/4455
See application file for complete search history.

(56) References Cited

U.S. PATENT DOCUMENTS

| | | | |
|---|---|---|---|
| 9,717,601 | B2 | 8/2017 | Miller |
| 9,801,733 | B2 | 10/2017 | Butler |
| 9,962,270 | B2 | 5/2018 | Alheidt |
| 10,034,769 | B2 | 7/2018 | Baynham |
| 10,278,831 | B2 | 5/2019 | Sandul |
| 10,299,934 | B2 | 5/2019 | Adams |
| 2011/0282453 | A1* | 11/2011 | Greenhalgh .......... A61F 2/4425 623/17.16 |
| 2013/0197647 | A1 | 8/2013 | Wolters et al. |
| 2014/0277139 | A1* | 9/2014 | Vrionis .............. A61B 17/8635 606/246 |
| 2015/0012097 | A1 | 1/2015 | Ibarra |
| 2017/0100255 | A1 | 4/2017 | Guy |
| 2018/0078384 | A1 | 3/2018 | Suddaby |
| 2018/0296361 | A1 | 10/2018 | Butler et al. |
| 2019/0021873 | A1* | 1/2019 | Dmuschewsky ..... A61F 2/4425 |
| 2019/0117409 | A1* | 4/2019 | Shoshtaev ............. A61F 2/4611 |
| 2019/0274837 | A1 | 9/2019 | Eisen et al. |

FOREIGN PATENT DOCUMENTS

| | | |
|---|---|---|
| CN | 107174383 A | 9/2017 |
| CN | 206659970 U | 11/2017 |
| CN | 107890384 A | 4/2018 |
| CN | 109820626 A | 5/2019 |
| TW | 201912120 A | 4/2019 |

OTHER PUBLICATIONS

Sevrain et al., "Biomechanical evaluation of predictive parameters of progression in adolescent isthmic spondylolisthesis: a computer modeling And simulation study" Jul. 2012.

Ansari et al., "Diagnosis of Vertebral Column Disorders Using Machine Learning Classifiers" May 2013.

Damasceno et al., "Lumbar Lordosis: A Study Of Angle Values and of Vertebral Bodies and Intervertebral Discs Role Luiz Henrique Fonseca Damascen" Apr. 2006.

Hegazy et al., "Midsagittal Anatomy of Lumbar Lordosis in Adult Egyptians: MRI Study" Aug. 2014.

Bailey et al., "Morphological and postural sexual dimorphism of the lumbar spine facilitates greater lordosis in Females" Feb. 2016.

Zubrzycki et al., "Numerical Analysis of Spinal Loads in Spondylolisthesis Treatment Using Pedicle Screws—Preliminary Research" Sep. 2017.

Hyun et al., "Predictive formula of ideal lumbar lordosis and lower lumbar lordosis determined by individual pelvic incidence in asymptomatic elderly population" Mar. 2019.

Yilgor MD et al., "Relative lumbar lordosis and lordosis distribution index individualized pelvic incidence-based proportional parameters that quantify lumbar lordosis more precisely than the concept of pelvic incidence minus lumbar lordosis" Aug. 2017.

Lafage et al., "Self-learning computers for surgical planning and prediction of postoperative alignment" Feb. 2018.

EP Search Report in Application No. 19219449.6 dated Jul. 17, 2020.

Taiwan Office Action issued in corresponding application No. 108140606, dated Nov. 30, 2020.

* cited by examiner

SPINAL INTERVERTEBRAL BODY FUSION DEVICE

CROSS-REFERENCE TO RELATED APPLICATIONS

This non-provisional application claims priority under 35 U.S.C. § 119(a) on Patent Application No(s). 108140606 filed in R.O.C. Taiwan on Nov. 8, 2019, the entire contents of which are hereby incorporated by reference.

TECHNICAL FIELD

The disclosure relates to an implant, more particularly to a spinal intervertebral body fusion device.

BACKGROUND

Between each vertebral body is a cushion called an intervertebral disc for absorbing the stress and shock the body incurs during movement and preventing the vertebrae from grinding against one another. Vertebral slippage (spondylolisthesis), displaced disc material (herniated intervertebral disc, HIVD), or spinal stenosis may be responsible for nerve compression and thus are common indications for discectomy surgery. The discectomy is a surgical procedure to remove herniated or degenerative disc material that is pressing on a nerve root or the spinal cord. The spinal fusion device is a replacement to be inserted into the intervertebral space during a spinal fusion procedure following the discectomy to prevent movement and to maintain the space originally occupied by the intervertebral disc. In order to restore and maintain the height of the intervertebral space and position of the vertebral body, the device implanted in the intervertebral space needs to be properly selected.

The conventional spinal fusions (also called cage, spacer, or structural graft) filled with local autogenous bone to be implanted in the disc space are unadjustable in size, which may result in some problems during the implantation. More specifically, the optimal size of the intervertebral space can be determined only during the operation, thus the cage often fail to satisfy the size requirement. As a result, the implanted device would be unable to provide sufficient support to the vertebral body and may fail to maintain the position of the vertebral body.

SUMMARY

The present disclosure provides a spinal intervertebral body fusion device having adjustable features making itself have an optimal size to restore and maintain the height of the intervertebral space and position of the vertebral body.

One embodiment of the disclosure provides a spinal intervertebral body fusion device including an adjustable spacer, a first pushing piece, a second pushing piece, and an operative piece. The adjustable spacer includes a first supporting plate portion and a second supporting plate portion. The first supporting plate portion is movably installed on the second supporting plate portion. The first supporting plate portion and the second supporting plate portion together form a first opening and a second opening which are respectively located at two opposite sides of the adjustable spacer. The first pushing piece is located at the first opening and partially located between and clamped by the first supporting plate portion and the second supporting plate portion. The second pushing piece located at the second opening and partially located between and clamped by the first supporting plate portion and the second supporting plate portion. The operative piece is located between the first supporting plate portion and the second supporting plate portion. The operative piece is movably disposed through the second pushing piece and screwed to the first pushing piece. When the operative piece is activated, the operative piece forces the second pushing piece and the first pushing piece to move towards or away from each other to change a relative position of the first supporting plate portion and the second supporting plate portion. The operative piece has an annular slot, and the second pushing piece is partially located in the annular slot.

According to the spinal intervertebral body fusion device discussed in the above embodiment of the disclosure, the first supporting plate portion and the second supporting plate portion are movably installed to each other and together clamp the first pushing piece and the second pushing piece respectively at the first opening and the second opening on opposite sides, thus the operative piece that is located between the first supporting plate portion and the second supporting plate portion and connected to the first pushing piece and the second pushing piece is able to force the first pushing piece and the second pushing piece to clamp the first supporting plate portion and the second supporting plate portion so as to force the first supporting plate portion and the second supporting plate portion to move away from each other, achieving the size adjustment of the spinal intervertebral body fusion device. As such, the spinal intervertebral body fusion device is able to be adjusted to an optimal size to restore and maintain the height of the intervertebral space and position of the vertebral body.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

Figure 1:
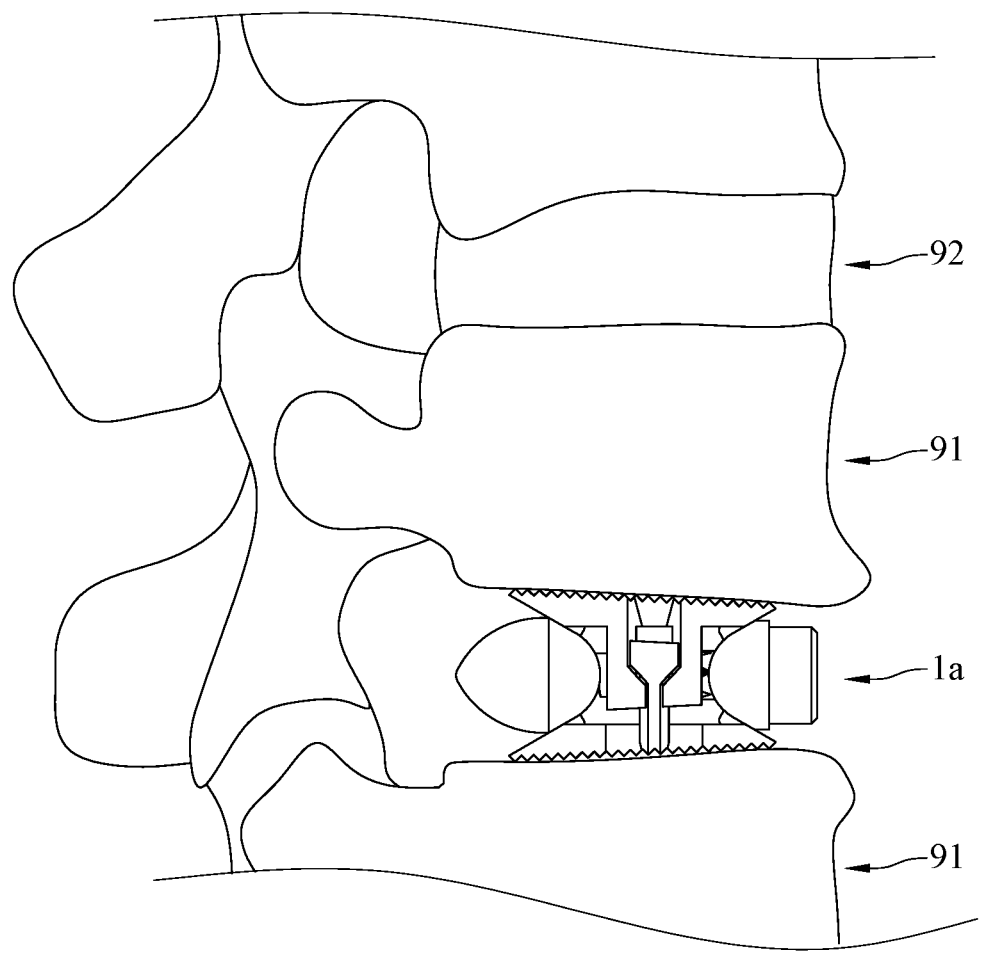
FIG. 1 depicts a scenario that a spinal intervertebral body fusion device according to one embodiment of the disclosure is implanted in an intervertebral space.

In the following detailed description, for purposes of explanation, numerous specific details are set forth in order to provide a thorough understanding of the disclosed embodiments. It will be apparent, however, that one or more embodiments may be practiced without these specific details.

In addition, for the purpose of simple illustration, well-known features may be drawn schematically, and some unnecessary details may be omitted from the drawings. And the size or ratio of the features in the drawings of the present disclosure may be exaggerated for illustrative purposes, but the present disclosure is not limited thereto. Note that the actual size and designs of the product manufactured based on the teaching of the present disclosure may also be properly modified according to any actual requirement.

Further, as used herein, the terms "end", "part", "portion" or "area" may be used to describe a technical feature on or between component(s), but the technical feature is not limited by these terms. In addition, unless otherwise specified, the term "substantially", "approximately" or" about" may be used herein to provide an industry-accepted tolerance to its corresponding term without resulting in a change in the basic function of the subject matter at issue.

Furthermore, unless otherwise defined, all the terms used in the disclosure, including technical and scientific terms, have their ordinary meanings that can be understood by those skilled in the art. Moreover, the definitions of the above terms are to be interpreted as being consistent with the technical fields related to the disclosure. Unless specifically defined, these terms are not to be construed as too idealistic or formal meanings.

Firstly, please refer to FIG. 1, a spinal intervertebral body fusion device 1a is provided. As shown, the spinal intervertebral body fusion device 1a is configured to be implanted into the space originally occupied by an intervertebral disc 92 between vertebral bodies 91; that is, the spinal intervertebral body fusion device 1a is able to replace the removed intervertebral disc 92 between the vertebral bodies 91. Particularly, the spinal intervertebral body fusion device 1a is able to be adjusted to an optimal size to restore and maintain the required height of the intervertebral space and required position of the vertebral body.

In this and some other embodiments, the spinal intervertebral body fusion device 1a may be, but not limited to, manufactured by 3D printing technology and its material is biocompatible and has sufficient rigidity to provide proper support to the vertebral body 91 and maintain the desired position of the vertebral body 91, such as titanium alloy, iron-based alloy, cobalt alloy, polymer material, ceramic or composite material thereof, but the disclosure is not limited thereto.

The spinal intervertebral body fusion device 1a is configured for vertebral body fusion. Note that the spinal intervertebral body fusion device 1a may have rough surfaces to aid the fusion process, but these features are omitted from the drawings for the purpose of simple illustration.

Figure 2:
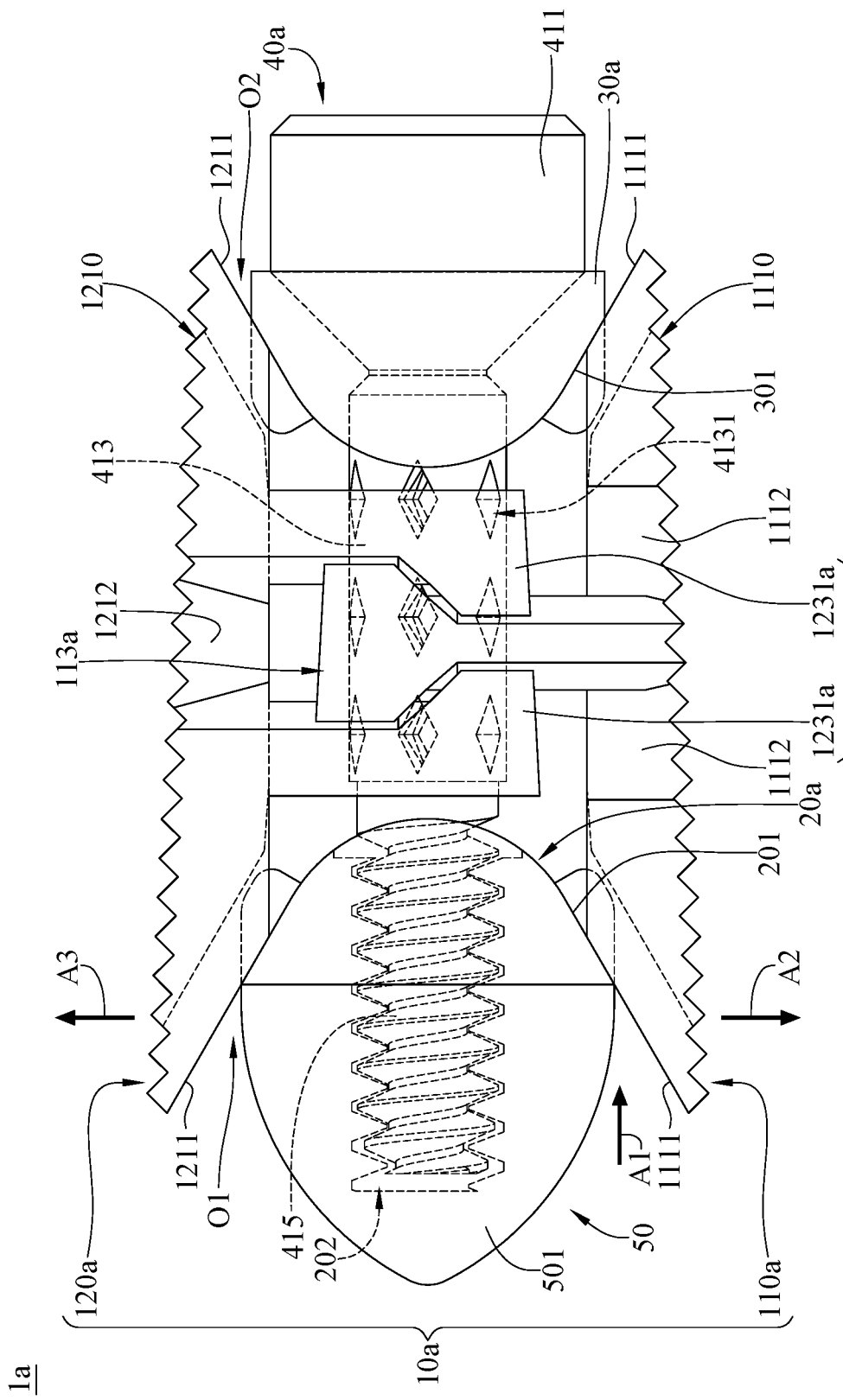
FIG. 2 is a side view of the spinal intervertebral body fusion device in FIG. 1.
Figure 3:
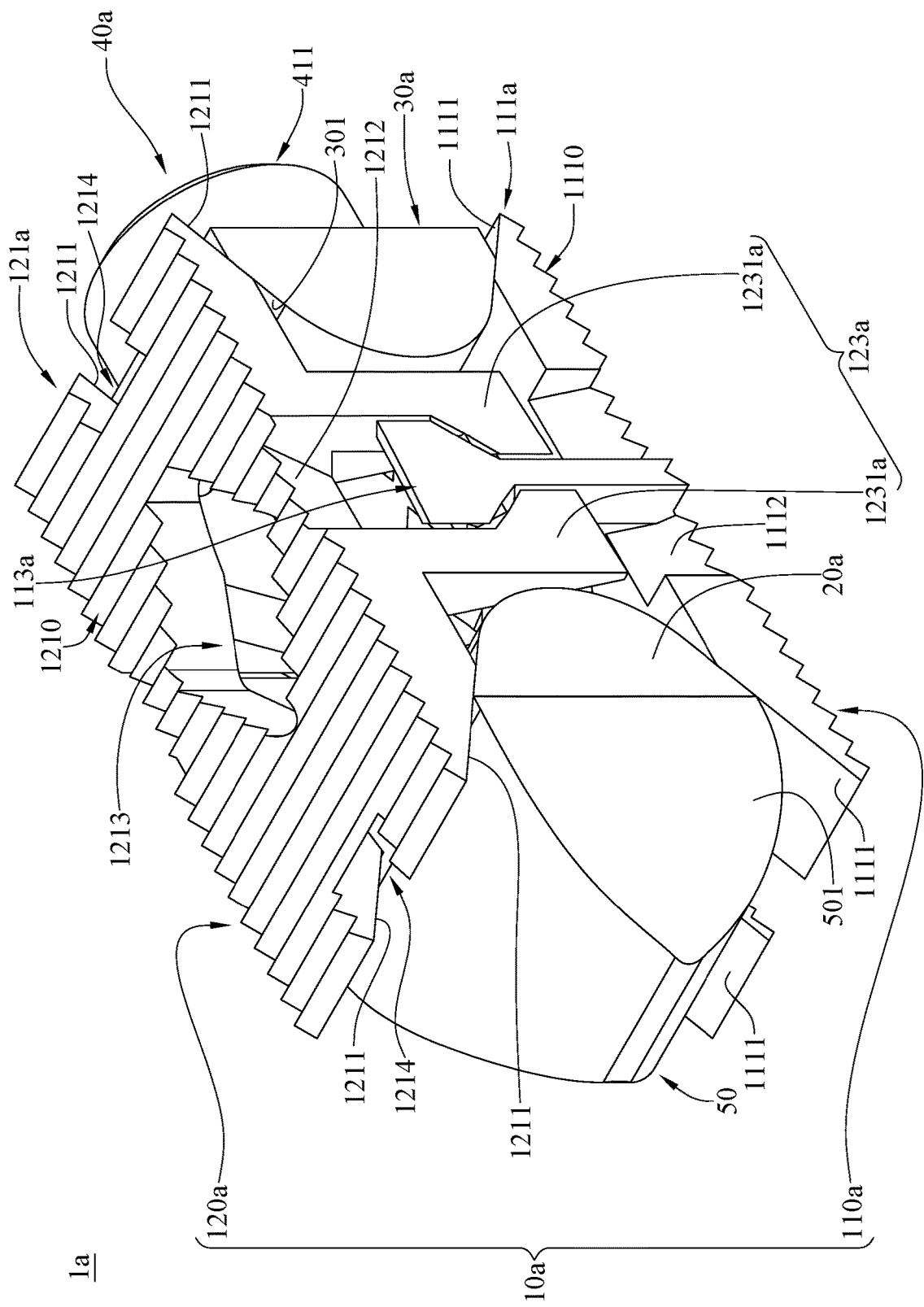
FIG. 3 is a perspective view of the spinal intervertebral body fusion device in FIG. 2.
Figure 4:
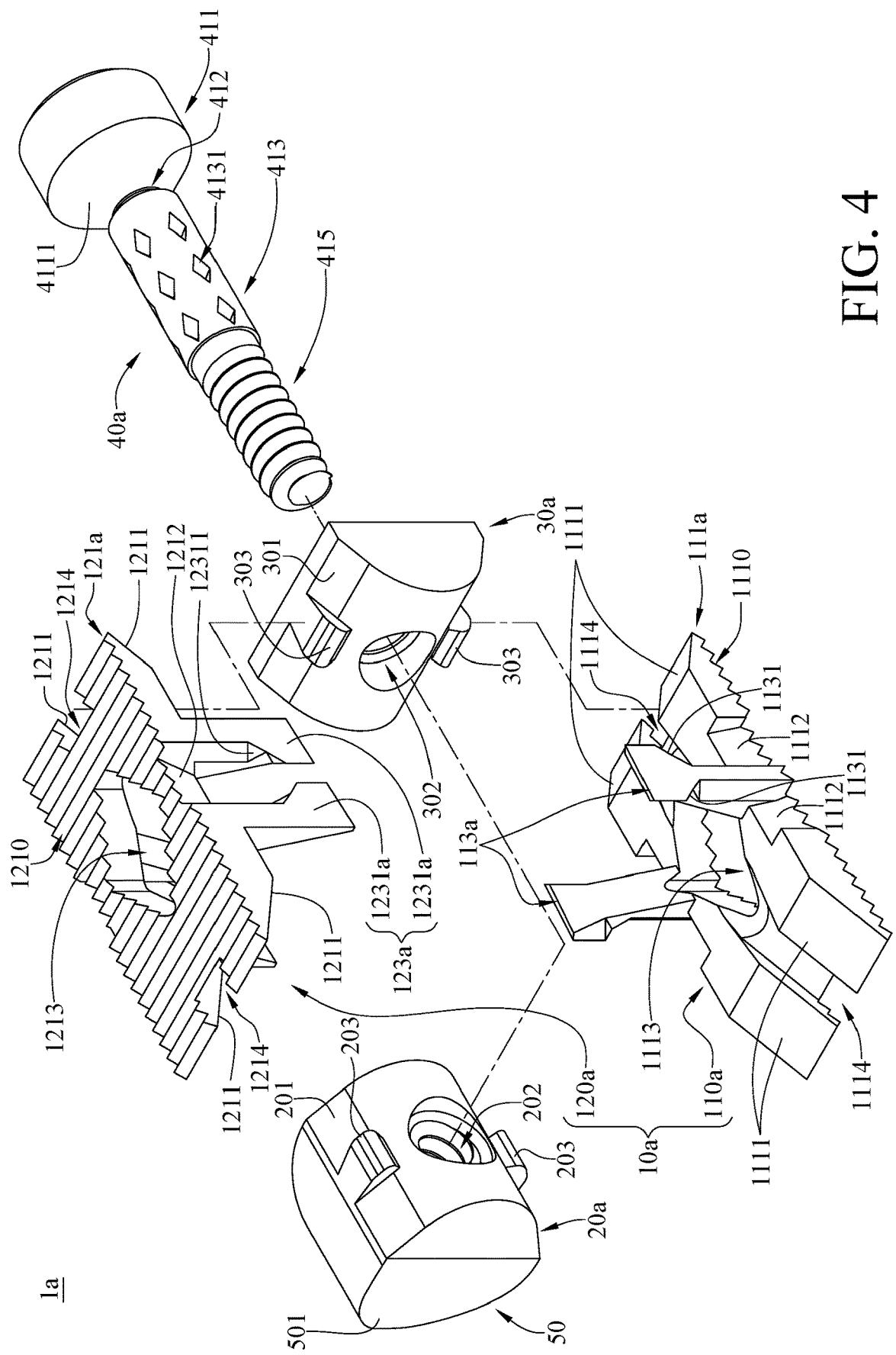
FIG. 4 is an exploded view of the spinal intervertebral body fusion device in FIG. 2.
Figure 5:
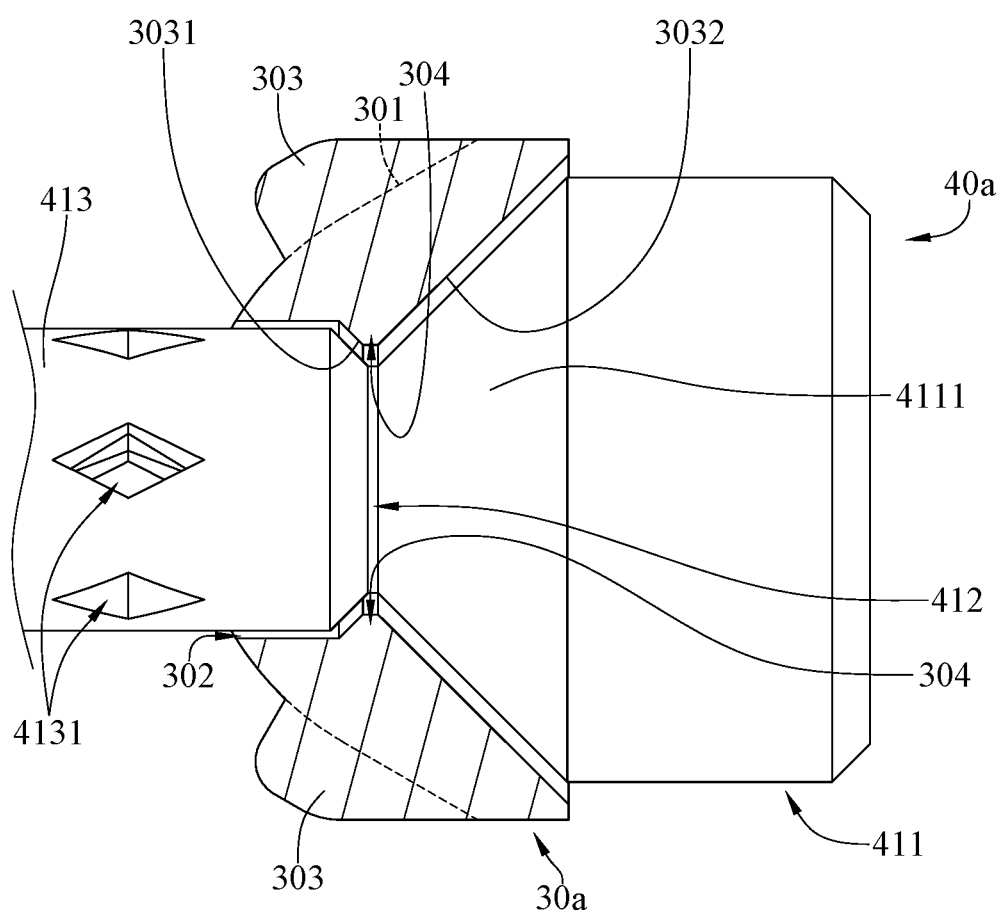
FIG. 5 is a partial enlarged view of the spinal intervertebral body fusion device in FIG. 2.

Also, the spinal intervertebral body fusion device 1a is adjustable in size and shape, allowing the surgeon to manually adjust it to fit the required disc space so as to provide proper support to the adjacent vertebral bodies 91 and maintain the desired position of the vertebral bodies 91. In detail, please refer to FIGS. 2-5, FIG. 2 is a side view of the spinal intervertebral body fusion device 1a in FIG. 1, FIG. 3 is a perspective view of the spinal intervertebral body fusion device 1a in FIG. 2, FIG. 4 is an exploded view of the spinal intervertebral body fusion device 1a in FIG. 2, and FIG. 5 is a partial enlarged view of the spinal intervertebral body fusion device in FIG. 2. In this and some other embodiments, the spinal intervertebral body fusion device 1a at least includes an adjustable spacer 10a, a first pushing piece 20a, a second pushing piece 30a, and an operative piece 40a.

The adjustable spacer 10a includes a first supporting body 110a and a second supporting body 120a. The first supporting body 110a and the second supporting body 120a are movably installed to each other. Specifically, in this embodiment, the first supporting body 110a includes a first supporting plate portion 111a and at least one first engagement arm portion 113a, the second supporting body 120a includes a second supporting plate portion 121a and at least one second engagement arm portion 123a, wherein the at least one second engagement arm portion 123a each have a pair of engaging structures 1231a spaced apart from each other.

As shown, in this embodiment, the first supporting body 110a includes two first engagement arm portions 113a respectively stand at two opposite sides of the first supporting plate portion 111a. However, the quantity of the first engagement arm portions of the first supporting body is not limited; in some other embodiments, the first supporting body may have only one first engagement arm portion. In addition, in this embodiment, the second supporting body 120a includes two second engagement arm portions 123a respectively stand at two opposite sides of the second supporting plate portion 121a. However, the quantity of the second engagement arm portion of the second supporting body is not limited; in some other embodiments, the second supporting body may have only one second engagement arm portion.

Figure 6:
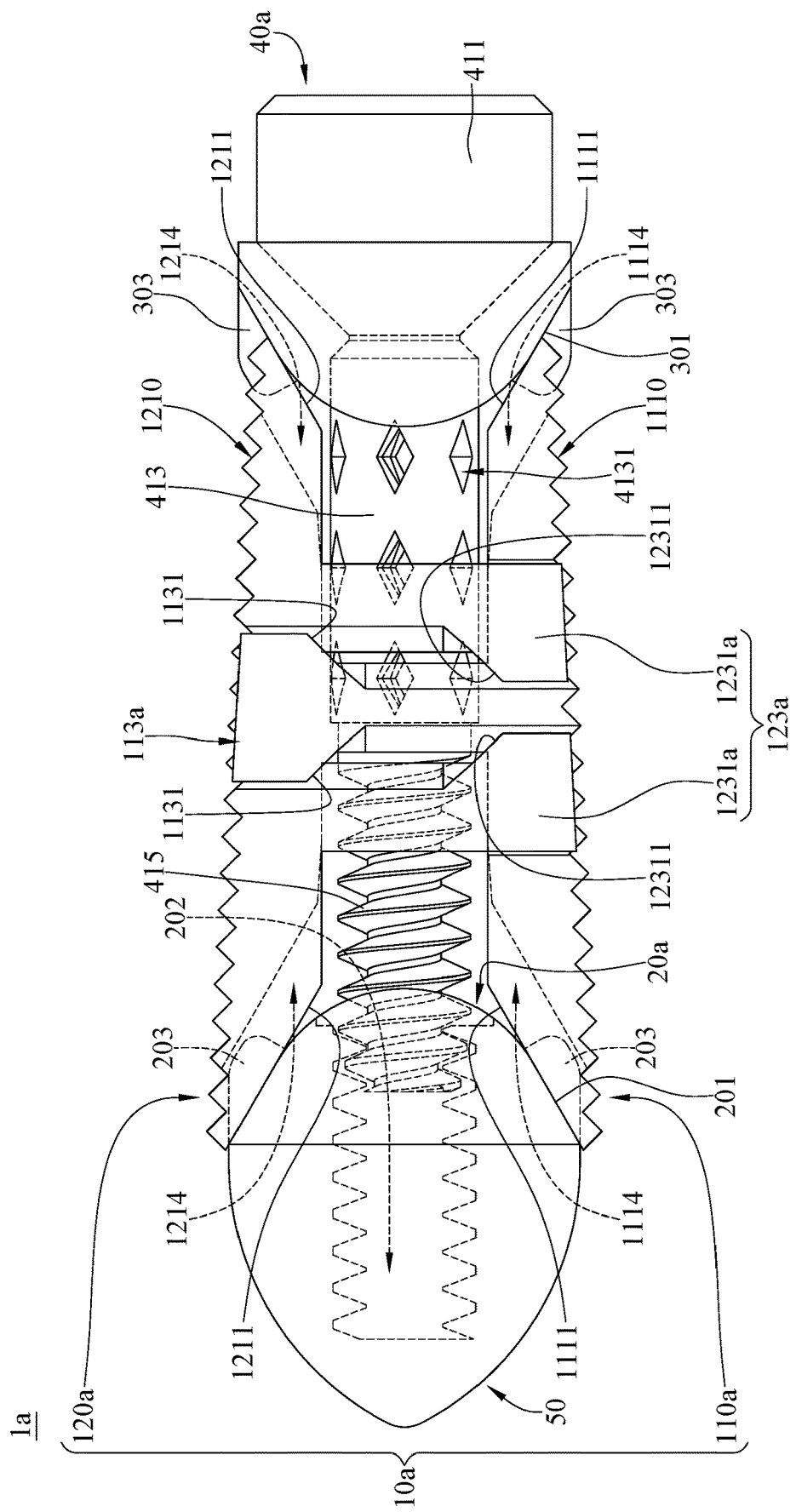
FIG. 6 depicts the spinal intervertebral body fusion device in FIG. 2 before the spinal intervertebral body fusion device is expanded.
Figure 7:
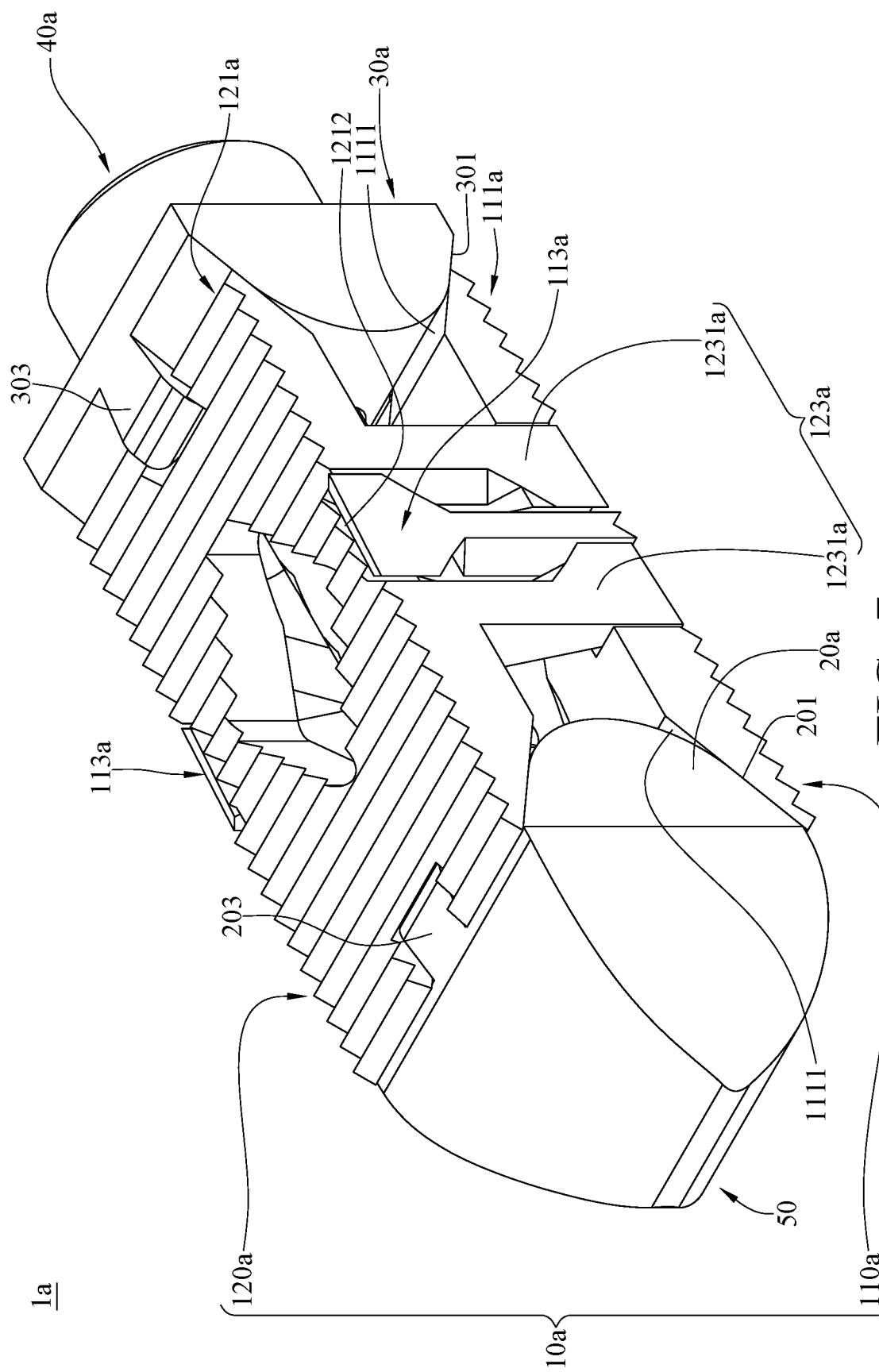
FIG. 7 is a perspective view of the spinal intervertebral body fusion device in FIG. 6.

In this and some other embodiments, the first engagement arm portion 113a of the first supporting body 110a is movably engaged into the gap between the engaging structures 1231a of the second engagement arm portion 123a of the second supporting body 120a, such that the first engagement arm portion 113a and the second engagement arm portion 123a are allowed to slide with each other along their extension directions. As such, the first supporting body 110a and the second supporting body 120a are movable toward or away from each other, making the adjustable spacer 10a switchable between an expanded status (as shown in FIGS. 1-2) and an unexpanded status (as shown in FIGS. 6-7 mentioned in later paragraphs).

Note that, in this and some other embodiments, the first supporting body 110a and the second supporting body 120a of the adjustable spacer 10a may be 3D printed in the same step; that is, the first supporting body 110a and the second supporting body 120a were 3D printed together. In such a case, the adjustable spacer 10a is 3D printed in a single process. Therefore, when the first supporting body 110a and the second supporting body 120a are formed, they also self-assemble to become the adjustable spacer 10a.

Herein, the usage of the spinal intervertebral body fusion device 1a may be used as a reference to define the spatial terms "front side" and "back side" used below. As shown in FIG. 1 or FIG. 2, the front side of the spinal intervertebral body fusion device 1a may indicate the left part of the figure, and the back side of the spinal intervertebral body fusion device 1a may indicate the right part of the figure. These spatial terms also apply to the components of the spinal intervertebral body fusion device 1a, but these terms are merely for the purpose of clear illustration, but disclosure is not limited thereto.

The cooperation of the first pushing piece 20a, the second pushing piece 30a, and operative piece 40a can achieve the status switching of the adjustable spacer 10a between the expanded status and the unexpanded status. In detail, in this and some other embodiments, the first supporting plate portion 111a of the first supporting body 110a of the adjustable spacer 10a has at least one first inclined contact surface 1111 respectively located at the front side and the back side of the first supporting plate portion 111a; the second supporting plate portion 121a of the second supporting body 120a of the adjustable spacer 10a has at least one second inclined contact surface 1211 respectively located at the front side and the back side of the second supporting plate portion 121a. In such an arrangement, the first supporting plate portion 111a and the second supporting plate portion 121a together form a first opening O1 and a second opening O2 respectively located at the front side and the back side of the adjustable spacer 10a, as shown in FIGS. 2-3, the first opening O1 and the second opening O2 are respectively located at two opposite sides of the adjustable spacer 10a and are tapered towards each other. Note that the size of the first opening O1 and the second opening O2 changes as the adjustable spacer 10a switches between the expanded status and the unexpanded status.

The first pushing piece 20a is located at the first opening O1. In this and some other embodiments, the first pushing piece 20a has a first push surface 201 configured to contact and push the first inclined contact surface 1111 of the first supporting plate portion 111a and the second inclined contact surface 1211 of the second supporting plate portion 121a that are located at the front side. The second pushing piece 30a is located at the second opening O2. In this and some other embodiments, the second pushing piece 30a has a second push surface 301 configured to contact and push the first inclined contact surface 1111 of the first supporting plate portion 111a and the second inclined contact surface 1211 of the second supporting plate portion 121a that are located at the back side. The operative piece 40a is movably disposed through a second mounting hole 302 of the second pushing piece 30a and the space (not numbered) between the first supporting plate portion 111a and the second supporting plate portion 121a, and is screwed to a first mounting hole 202 of the first pushing piece 20a. When the operative piece 40a is forced to rotate with respect to the adjustable spacer 10a, the operative piece 40a is able to force the first pushing piece 20a and the second pushing piece 30a to move away from each other so as to switch the adjustable spacer 10a from the expanded status to the unexpanded status.

In more detail, in this and some other embodiments, the operative piece 40a is an integrally formed single piece and at least includes a head portion 411, a neck portion 413, and a threaded portion 415. The head portion 411 is located at the back side of the spinal intervertebral body fusion device 1a and is configured for the surgeon to manually operate the spinal intervertebral body fusion device 1a. The neck portion 413 is connected to and located between the head portion 411 and the threaded portion 415. Part of the head portion 411 and part of the neck portion 413 are disposed through the second mounting hole 302 of the second pushing piece 30a. The other part of the neck portion 413 is accommodated in the space between the first supporting plate portion 111a and the second supporting plate portion 121a. In this or some other embodiments, the neck portion 413 has pores 4131, and the pores 4131 allow the nearby tissues to grow into the spinal intervertebral body fusion device 1a so as to aid the fusion process. Note that the size and shape of the pores 4131 and the distance among the pores 4131 are not limited and may be modified according to actual requirements. In some embodiments, the head portion 411 of the operative piece 40a may also have the pores 4131 to further aid the fusion process.

The threaded portion 415 has an external thread (not numbered) and is configured to be screwed into the first mounting hole 202 of the first pushing piece 20a. As shown, there is an internal thread (not numbered) in the first mounting hole 202 for the engagement with the threaded portion 415 of the operative piece 40a.

In addition, as shown in FIG. 5, in this and some other embodiments, the head portion 411 of the operative piece 40a has an engaging surface 4111 facing towards the adjustable spacer 10a, the second pushing piece 30a has an annular protrusion 304 located in the second mounting hole 302 and radially extending towards the center (not numbered) of the second mounting hole 302, the annular protrusion 304 has an inner engaging surface 3031 and an outer engaging surface 3032 respectively located at a side of the annular protrusion 304 closer to the first pushing piece 20a and a side of the annular protrusion 304 away from the first pushing piece 20a. The second mounting hole 302 is substantially an hourglass-shaped hole. It is understood that both of the inner engaging surface 3031 and the outer engaging surface 3032 are inclined surfaces. The inner engaging surface 3031 of the annular protrusion 304 of the second pushing piece 30a is configured to contact and push the neck portion 413 of the operative piece 40a, and the engaging surface 4111 of the head portion 411 of the operative piece 40a is configured to contact and push the outer engaging surface 3032 of the annular protrusion 304 of the second pushing piece 30a. In such an arrangement, at least part of the annular protrusion 304 is located in an annular slot (it can also be considered as a circular slot) 412 formed by the engaging surface 4111 of the head portion 411 and the neck portion 413. The annular slot 412 does not allow the second pushing piece 30a to move in an extension direction of the operative piece 40a, but the operative piece 40a is allowed to rotate with respect to the second pushing piece 30a. That is, the operative piece 40a is rotatably disposed through the second pushing piece 30a, is unable to move along the operative piece 40a. Therefore, the operative piece 40a can move the second pushing piece 30a forward and backward together.

In this and some other embodiments, the second pushing piece 30a and the operative piece 40a may be 3D printed in the same step; that is, the second pushing piece 30a and the operative piece 40a were 3D printed together at the same time. As such, when the second pushing piece 30a and the operative piece 40a are formed, they also self-assemble to form the arrangement shown in FIG. 5.

Herein, please refer to FIG. 2 and FIGS. 4-5, when the operative piece 40a is rotated in a way to gradually screw the threaded portion 415 into the first mounting hole 202 of the first pushing piece 20a, the operative piece 40a is rotated with respect to the second pushing piece 30a and the first pushing piece 20a, but the second pushing piece 30a presses against the first inclined contact surface 1111 of the first supporting plate portion 111a and the second inclined contact surface 1211 of the second supporting plate portion 121a and is unable to move along the operative piece 40a, thus this movement of the operative piece 40a will pull the first pushing piece 20a towards the second pushing piece 30a, as the arrow A1 shown in FIG.

By doing so, the first push surface 201 of the first pushing piece 20a and the second push surface 301 of the second pushing piece 30a can clamp and push the first inclined contact surfaces 1111 of the first supporting plate portion 111a of the first supporting body 110a and the second inclined contact surfaces 1211 of the second supporting plate portion 121a of the second supporting body 120a, since the first push surface 201 and the second push surface 301 and the first inclined contact surface 1111 and the second inclined contact surface 1211 are all inclined surfaces, thus the first pushing piece 20a and the second pushing piece 30a which gradually move toward each other can force the first supporting plate portion 111a of the first supporting body 110a and the second supporting plate portion 121a of the second supporting body 120a to move away from each other, as the arrows A2 and A3 shown in FIG. 2. During this movement, the first engagement arm portion 113a of the first supporting body 110a and the second engagement arm portion 123a of the second supporting body 120a are moved along each other so as to ensure the predetermined paths of the first supporting plate portion 111a and the second supporting plate portion 121a.

It is understood that the distance between the first supporting plate portion 111a of the first supporting body 110a and the second supporting plate portion 121a of the second supporting body 120a can be adjusted by rotating the operative piece 40a to change the relative position of the first pushing piece 20a and the second pushing piece 30a. In this or some other embodiments, the end portion of the first engagement arm portion 113a has at least one first stopping surface 1131, and the end portion of the engaging structure 1231a of the second engagement arm portion 123a has a second stopping surface 12311, where the first stopping surface 1131 substantially faces away from the second supporting plate portion 121a of the second supporting body 120a, and the second stopping surface 12311 substantially faces away from the first supporting plate portion 111a of the first supporting body 110a. Therefore, when the distance of the first supporting plate portion 111a of the first supporting body 110a and the second supporting plate portion 121a of the second supporting body 120a is increased to a specific value, the first stopping surfaces 1131 of the first engagement arm portions 113a press against the second stopping surfaces 12311 of the engaging structures 1231a of the second engagement arm portions 123a, which prevents the first supporting plate portion 111a of the first supporting body 110a and the second supporting plate portion 121a of the second supporting body 120a from moving further away from each other, that is, the first stopping surfaces 1131 and the second stopping surfaces 12311 limits the maximum adjustment range of the adjustable spacer 10a.

Accordingly, the surgeon is allowed to simply rotate the operative piece 40a to adjust the size of the spinal intervertebral body fusion device 1a to fit the required disc space. This not only facilitates the implantation operation but also provides proper support to the vertebral body and maintains the desired position of the vertebral body. Also, the cooperation of the operative piece 40a and the first pushing piece 20a achieves a stepless adjustment of the size of the spinal intervertebral body fusion device 1a, enabling a precise adjustment of the size of the spinal intervertebral body fusion device 1a to provide optimal support to the adjacent vertebral bodies.

Note that the inclinations of the first push surface 201 of the first pushing piece 20a, the second push surface 301 of the second pushing piece 30e, and the first inclined contact surface 1111 and the second inclined contact surface 1211 of the adjustable spacer 10a are not limited and may be modified according to the actual requirements.

In addition, in this and some other embodiments, the first pushing piece 20a has at least one first protrusion 203, and the second pushing piece 30e has at least one second protrusion 304. The first supporting plate portion 111a of the first supporting body 110a further has at least one recess 1114 respectively formed on the first inclined contact surfaces 1111, the second supporting plate portion 121a of the second supporting body 120a further has at least one recess 1214 respectively formed on the second inclined contact surfaces 1211. The first protrusions 203 are respectively located on two opposite sides of the first push surface 201 of the first pushing piece 20a relative close to the first supporting plate portion 111a and the second supporting plate portion 121a and respectively located in the recess 1114 and the recess 1214 at the front side. In this arrangement, the first pushing piece 20a is not allowed to move in a direction perpendicular to the extension direction of the operative piece 40a. The second protrusions 303 are respectively located on two opposite sides of the second push surface 301 of the second pushing piece 30a relative close to the first supporting plate portion 111a and the second supporting plate portion 121a and respectively located in the recess 1114 and the recess 1214 at the back side. In this arrangement, the second pushing piece 30a is either not allowed to move in a direction perpendicular to the extension direction of the operative piece 40a.

In addition, in this and some other embodiments, the first supporting plate portion 111a of the first supporting body 110a has a plurality of first protrusion 1110 formed on a side of the first supporting plate portion 111a facing away from the second supporting plate portion 121a, and the second supporting plate portion 121a of the second supporting body 120a has a plurality of second protrusions 1210 formed on the side of the second supporting plate portion 121a facing away from the first supporting plate portion 111a. The first protrusions 1110 and the second protrusions 1210 can increase the contact area of the spinal intervertebral body fusion device 1a and the adjacent vertebral bodies 91 to improve the fusion process. Note that the shape and size of the first protrusions 1110 and the second protrusions 1210 are not limited.

Further, in this or some other embodiments, the first supporting plate portion 111a of the first supporting body 110a of the adjustable spacer 10a may have at least one first passage 1113, and the second supporting plate portion 121a of the second supporting body 120a of the adjustable spacer 10a may have at least one second passage 1213. The first passage 1113 and the second passage 1213 are connected to the space between the first supporting plate portion 111a and the second supporting plate portion 121a, which allows the nearby tissues to grow into the space and reach the features in the space, such as the neck portion 413 and the threaded portion 415 of the operative piece 40a, but the disclosure is not limited thereto.

Moreover, in some embodiments, the first supporting body 110a and the second supporting body 120a of the adjustable spacer 10a may also have pores (not shown) to allow the nearby tissues to grow into the spinal intervertebral body fusion device 1a to further aid the fusion process. In some other embodiments, the spinal intervertebral body fusion device may have a porosity of approximately 20%-60%, but the disclosure is not limited thereto.

In addition, in this and some other embodiments, the spinal intervertebral body fusion device 1a has a leading end 50 to facilitate the insertion of the spinal intervertebral body fusion device 1a into the space between the vertebral bodies 91. The leading end 50 is located at the side of the first pushing piece 20a facing away from the second pushing piece 30a. The leading end 50 and the first pushing piece 20a may be an integrally formed single piece. The leading end 50 may have a leading structure 501 protruding in a direction away from the second pushing piece 30a and in a shape suitable for invading the space between the vertebral bodies 91, facilitating the placement of the spinal intervertebral body fusion device 1a.

In addition, to aid the fusion process of the spinal intervertebral body fusion device 1a and the adjacent vertebral bodies 91, the first supporting body 110a and the second supporting body 120a of the adjustable spacer 10a may be in shape and size substantially matching the contour of the vertebral bodies 91, but the disclosure is not limited thereto. Note that the size and shape of the first supporting body, the second supporting body and the other components of the spinal intervertebral body fusion device are not particularly limited. In short, the overall size and shape, such as length, width, height or proportion, of the spinal intervertebral body fusion device are not particularly limited and may be modified according to actual requirements.

Please refer to FIG. 2 or 4 and further refer to FIGS. 6-7 to introduce the unexpanded status of the spinal intervertebral body fusion device 1a, where FIG. 6 depicts the spinal intervertebral body fusion device 1a in FIG. 2 before the spinal intervertebral body fusion device is expanded, and FIG. 7 is a perspective view of the spinal intervertebral body fusion device 1a in FIG. 6. As shown, as the spinal intervertebral body fusion device 1a is in the unexpanded status, the first supporting plate portion 111a of the first supporting body 110a and the second supporting plate portion 121a of the second supporting body 120a are in a position to be able to engage with each other, such that the spinal intervertebral body fusion device 1a is able to stay in the current status by itself.

In detail, in this or some other embodiments, the first supporting plate portion 111a of the first supporting body 110a of the adjustable spacer 10a further has at least one first inclined stopping surface 1112 respectively located at two opposite sides of the first engagement arm portion 113a and respectively corresponding to the engaging structures 1231a of the second engagement arm portion 123a of the second supporting body 120a. From the viewpoint of FIG. 2, the end of the second engagement arm portion 123a is located between the second supporting plate portion 121a and the first inclined stopping surfaces 1112, thus the first inclined stopping surfaces 1112 are at the end of the travel path of the second engagement arm portion 123a. The second supporting plate portion 121a of the second supporting body 120a of the adjustable spacer 10a further has at least one second inclined stopping surface 1212 located between the engaging structures 1231a and corresponding to the first engagement arm portion 113a. From the viewpoint of FIG. 2, the end of the first engagement arm portion 113a is located between the first supporting plate portion 111a and the second inclined stopping surface 1212, thus the second inclined stopping surface 1212 is located at the end of the travel path of the first engagement arm portion 113a.

In such an arrangement, when the threaded portion 415 of the operative piece 40a is gradually removed out of the first mounting hole 202 of the first pushing piece 20a to make the first pushing piece 20a and the second pushing piece 30a move away from each other, the first supporting plate portion 111a and the second supporting plate portion 121a of the adjustable spacer 10a are allowed to move towards each other, such that the adjustable spacer 10a can be switched to the unexpanded status. In the unexpanded status, the first engagement arm portions 113a of the first supporting body 110a press against the second inclined stopping surfaces 1212 of the second supporting plate portion 121a of the second supporting body 120a, and the engaging structures 1231a of the second engagement arm portions 123a of the second supporting body 120a presses against the first inclined stopping surfaces 1112 of the first supporting plate portion 111a of the first supporting body 110a. The friction between the first engagement arm portions 113a and the second inclined stopping surfaces 1212 and the engaging structures 1231a and the first inclined stopping surfaces 1112 may cause the first supporting body 110a and the second supporting body 120a of the adjustable spacer 10a to temporarily fix to each other. This makes the spinal intervertebral body fusion device 1a stay in the current status itself. Also, the first inclined stopping surfaces 1112 can stop the second engagement arm portion 123a from sticking out of the outer surface of the first supporting plate portion 111a, and the second inclined stopping surfaces 1212 can stop the first engagement arm portions 113a from sticking out of the outer surface of the second supporting plate portion 121a.

Accordingly, before the usage of the spinal intervertebral body fusion device 1a, the spinal intervertebral body fusion device 1a is able to stay in the unexpanded status by itself. In the unexpanded status, the spinal intervertebral body fusion device 1a is in its possible smallest volume, and its components are all fixed to one another. Therefore, the spinal intervertebral body fusion device 1a in the unexpanded status is much compact in size so that it is good for storage and carry. In some applications, the first inclined stopping surfaces 1112 and the second inclined stopping surfaces 1212 may be approximately at 80-95 degrees respectively to the first supporting plate portion 111a and the second supporting plate portion 121a, but the inclinations of the first inclined stopping surfaces 1112 and the second inclined stopping surfaces 1212 are not limited and may be modified according to actual requirements.

As such, the spinal intervertebral body fusion device 1a has a certain amount of change in its shape for achieving the purpose of fitting the required disc space between the vertebral bodies. Note that, according to the requirement of the space between the vertebral bodies, the lengths of the first engagement arm portion, the second engagement arm portion, and/or the operative piece may be modified to obtain a proper adjustment range of the spinal intervertebral body fusion device. In some embodiments of the disclosure, the height of the spinal intervertebral body fusion device, from the unexpanded status to the expanded status, may increase from approximately 5 millimeters to 8 millimeters; that is, the spinal intervertebral body fusion device at least has approximately 3 millimeters of change in height. In another embodiment, the height of the spinal intervertebral body fusion device, from the unexpanded status to the expanded status, may increase from approximately 9 millimeters to 12 millimeters or from approximately 13 millimeters to 16 millimeters. Herein, the height indicates the furthest distance between the first supporting plate portion of the first supporting body and the second supporting plate portion of the second supporting body which are located on the same side (e.g., the front side or back side), meaning the farthest distance that the spinal intervertebral body fusion device can separate the adjacent vertebral bodies.

Further, the spinal intervertebral body fusion device $1a$ can also be used to correct the spinal-related symptoms, such as lordosis. In detail, as shown in FIG. 2, in this embodiment, the thicknesses of the first supporting plate portion $111a$ of the first supporting body $110a$ and the second supporting plate portion $121a$ of the second supporting body $120a$ decrease from the first opening O1 toward the second opening O2, such that the spinal intervertebral body fusion device $1a$ is tapered from the front side towards the back side. In such a configuration, the spinal intervertebral body fusion device $1a$ is able to push the vertebral bodies 91 to the desired positions to improve the lordosis.

Figure 8:
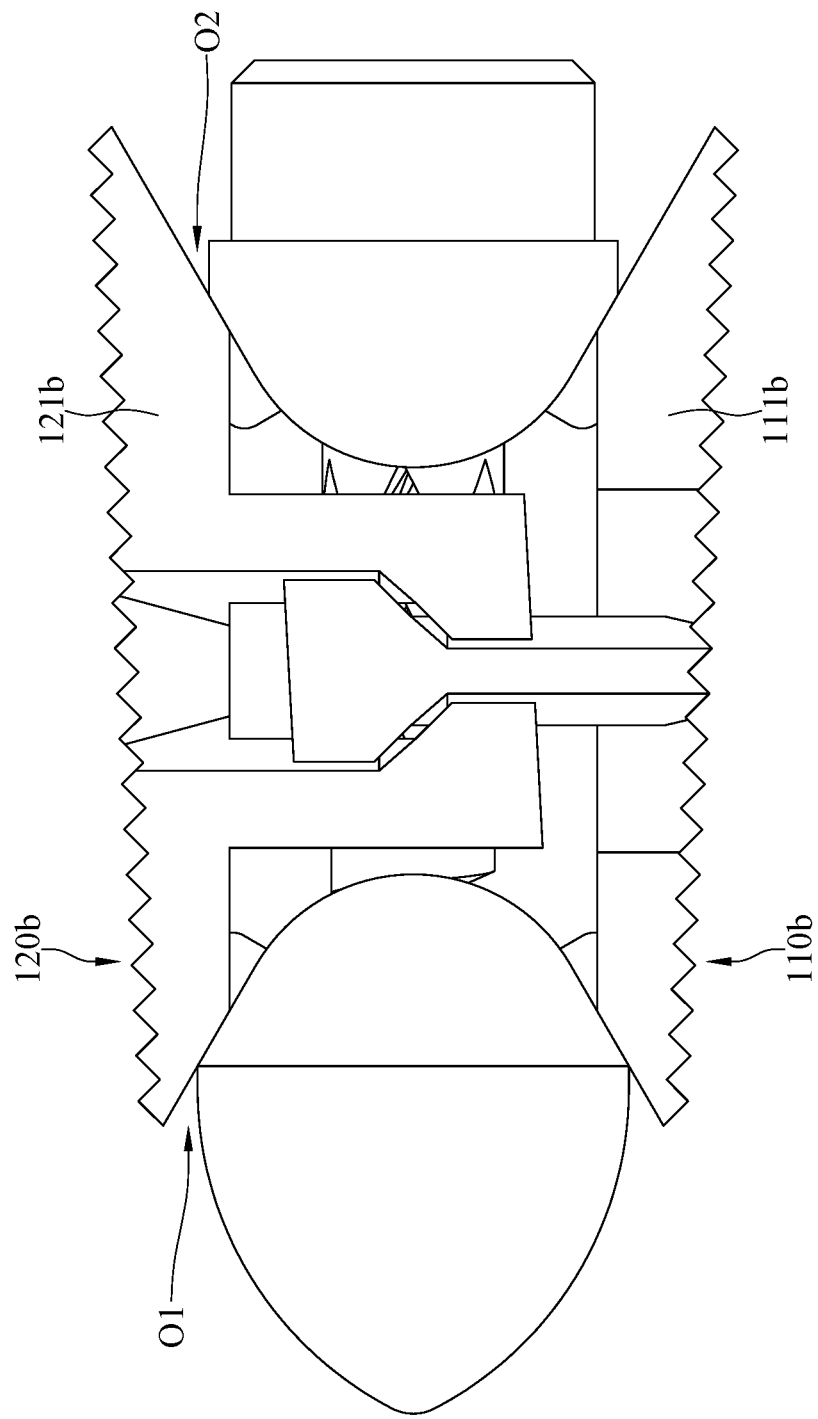
FIG. 8 is a side view of a spinal intervertebral body fusion device according to another embodiment of the disclosure.

The spinal intervertebral body fusion device is not restricted to be shaped for the lordosis. For example, please refer to FIG. 8, a spinal intervertebral body fusion device $1b$ is provided for correcting kyphosis. One of the main differences between this and the previous embodiments is the thickness of the first and second supporting bodies, thus the same and similar parts will not be repeated hereinafter. In this embodiment, the thicknesses of a first supporting plate portion $111b$ of a first supporting body $110b$ and a second supporting plate portion $121b$ of a second supporting body $120b$ increase from the first opening O1 towards the second opening O2, such that the spinal intervertebral body fusion device $1b$ is tapered from the back side towards the front side. In such a configuration, the spinal intervertebral body fusion device $1b$ is able to push the vertebral bodies 91 to the desired positions to improve the kyphosis.

Figure 9:
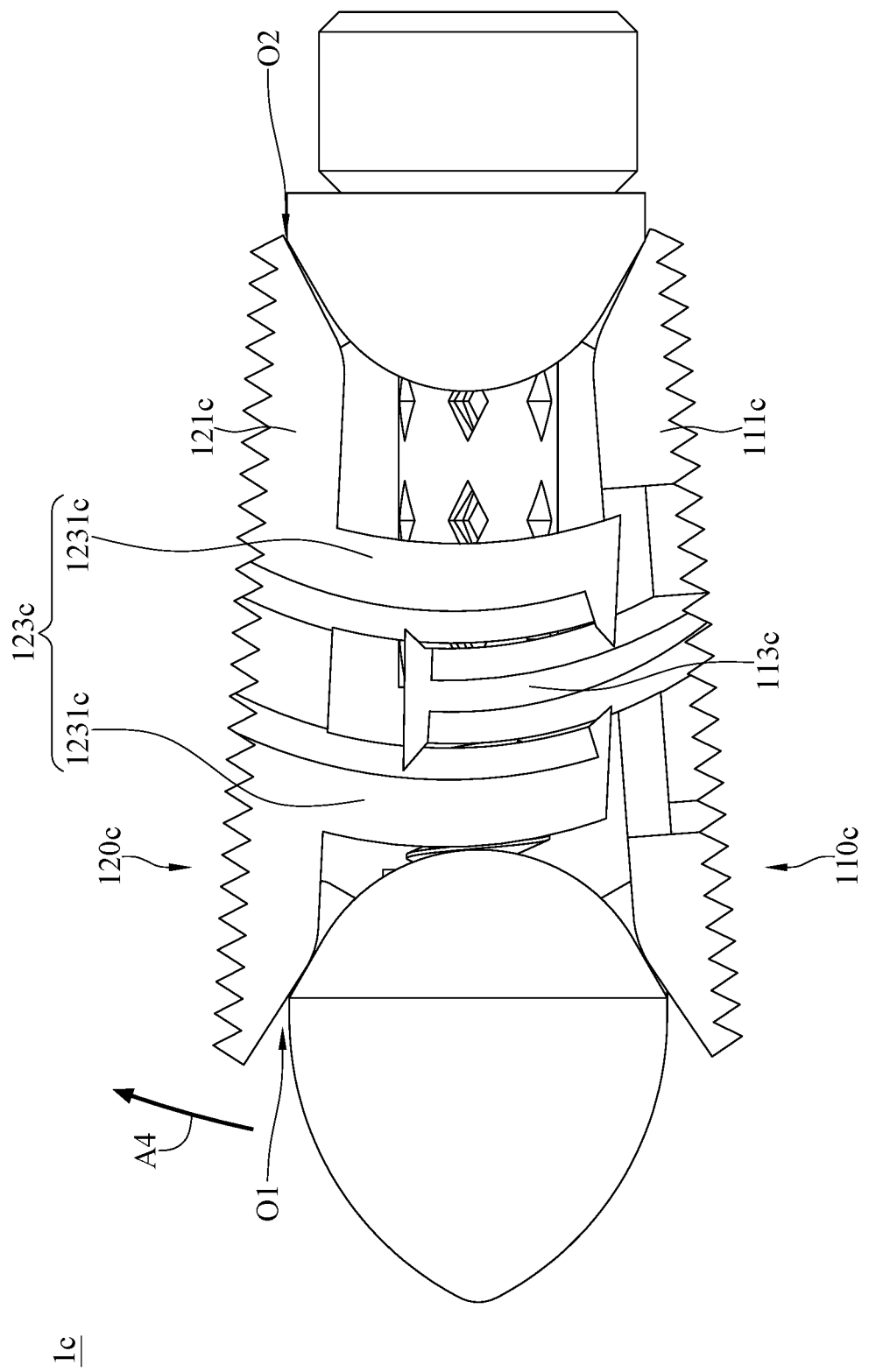
FIG. 9 is a side view of a spinal intervertebral body fusion device according to still another embodiment of the disclosure.

As discussed above, since the first supporting plate portion and the second supporting plate portion have thickness variations from the first opening to the second opening, the first engagement arm portion and the second engagement arm portion are required to linearly move with respect to each other to correct the lordosis or kyphosis, but the disclosure is not limited thereto. Please refer to FIG. 9, FIG. 9 is a side view of a spinal intervertebral body fusion device $1c$ according to still another embodiment of the disclosure. For the purpose of simple description, only the differences between this and the previous embodiments will be illustrated below, and the same and similar parts can be obtained with the reference of the aforementioned discussions.

As shown in FIG. 9, from the first opening O1 to the second opening O2 of the spinal intervertebral body fusion device $1c$, the thicknesses of a first supporting plate portion $111c$ and a second supporting plate portion $121c$ do not change. In such a configuration, first engagement arm portions $113c$ of a first supporting body $110c$ may extend in a curved manner, and engaging structures $1231c$ of second engagement arm portions $123c$ of a second supporting body $120c$ may extend in a curved manner corresponding to the shape of the first engagement arm portions $113c$. The cooperation of the first engagement arm portions $113c$ and the second engagement arm portions $123c$ enables the inclination adjustment of the second supporting plate portion $121c$ with respect to the first supporting plate portion $111c$, as the arrow A4 shown in FIG. 9. Therefore, during the movement of the spinal intervertebral body fusion device $1c$ from the unexpanded status to the expanded status, the change of the first opening O1 is greater than that of the second opening O2, and the spinal intervertebral body fusion device $1c$ forms a shape tapered from the front side to the back side. Similar to the aforementioned spinal intervertebral body fusion device $1a$, the spinal intervertebral body fusion device $1c$ is also able to push the vertebral bodies 91 to the desired positions to improve the lordosis. In one embodiment, the second supporting plate portion $121c$ may be moved to be at approximately 10 degrees to the first supporting plate portion $111c$.

Figure 10:
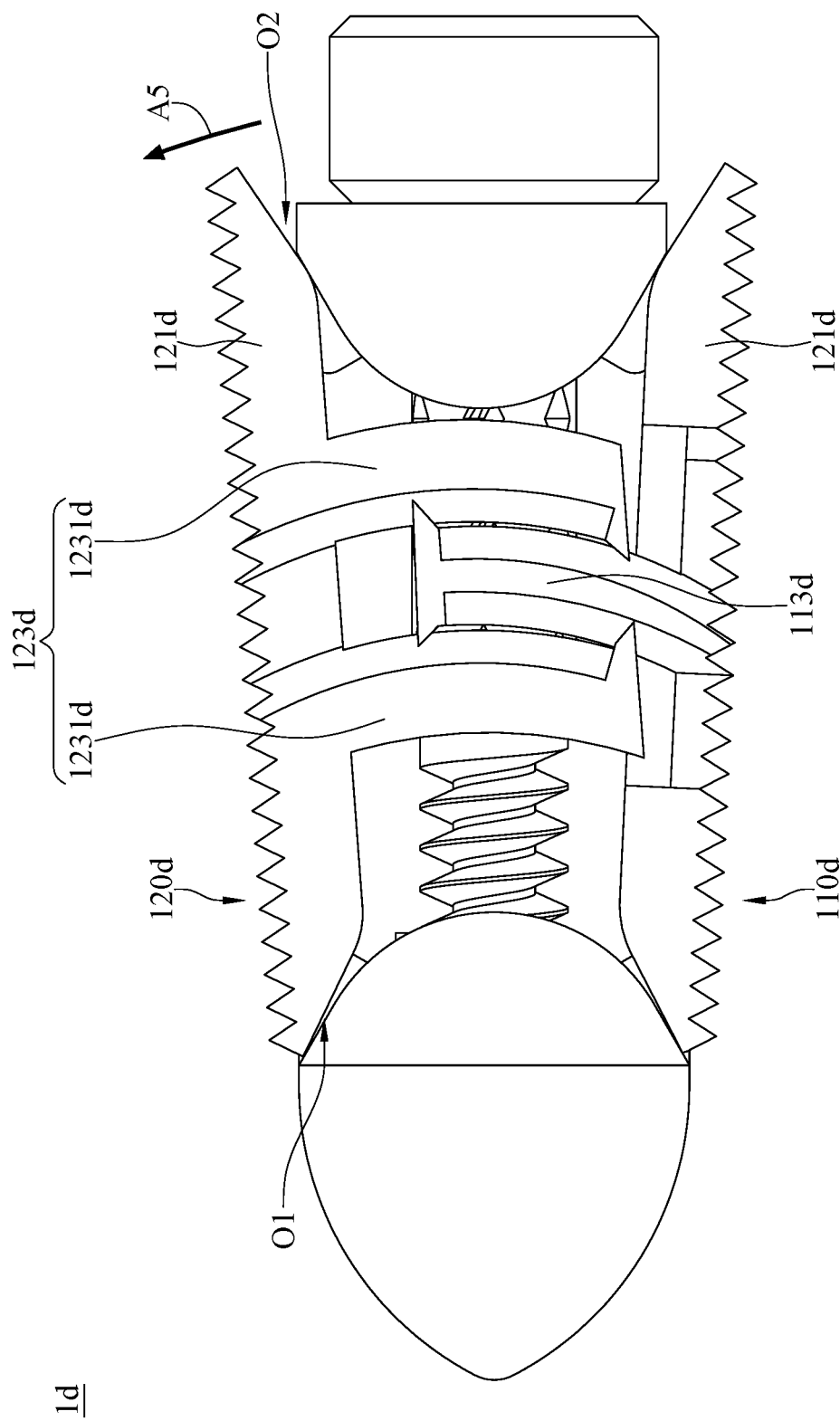
FIG. 10 is a side view of a spinal intervertebral body fusion device according to still yet another embodiment of the disclosure.

Alternatively, please refer to FIG. 10, FIG. 10 is a side view of a spinal intervertebral body fusion device $1d$ according to still yet another embodiment of the disclosure. For the purpose of simple description, only the differences between this and the previous embodiments will be illustrated below, and the same and similar parts can be obtained with the reference of the aforementioned discussions. As shown in FIG. 10, in the spinal intervertebral body fusion device $1d$, first engagement arm portions $113d$ of a first supporting body $110d$ extend in a curved manner which is opposite to that of the first engagement arm portion $113c$ in FIG. 9, and engaging structures $1231d$ of second engagement arm portions $123d$ of a second supporting body $120d$ extend in a curved manner which is corresponding to the shape of the first engagement arm portions $113d$ but is opposite to that of the second engagement arm portion $123c$ in FIG. 9. The cooperation of the first engagement arm portions $113d$ and the second engagement arm portions $123d$ also enables the inclination adjustment of the second supporting plate portion $121d$ with respect to the first supporting plate portion $111d$, as the arrow A5 shown in FIG. 10. During the movement of the spinal intervertebral body fusion device $1d$ from the unexpanded status to the expanded status, the change of the first opening O1 is smaller than that of the second opening O2, and the spinal intervertebral body fusion device $1d$ forms a shape tapered from the back side to the front side. Similar to the aforementioned spinal intervertebral body fusion device $1b$, the spinal intervertebral body fusion device $1d$ is also able to push the vertebral bodies 91 to the desired positions to improve the kyphosis. In one embodiment, the second supporting plate portion $121d$ may be moved to be at approximately 10 degrees to the first supporting plate portion $111d$.

Figure 11:
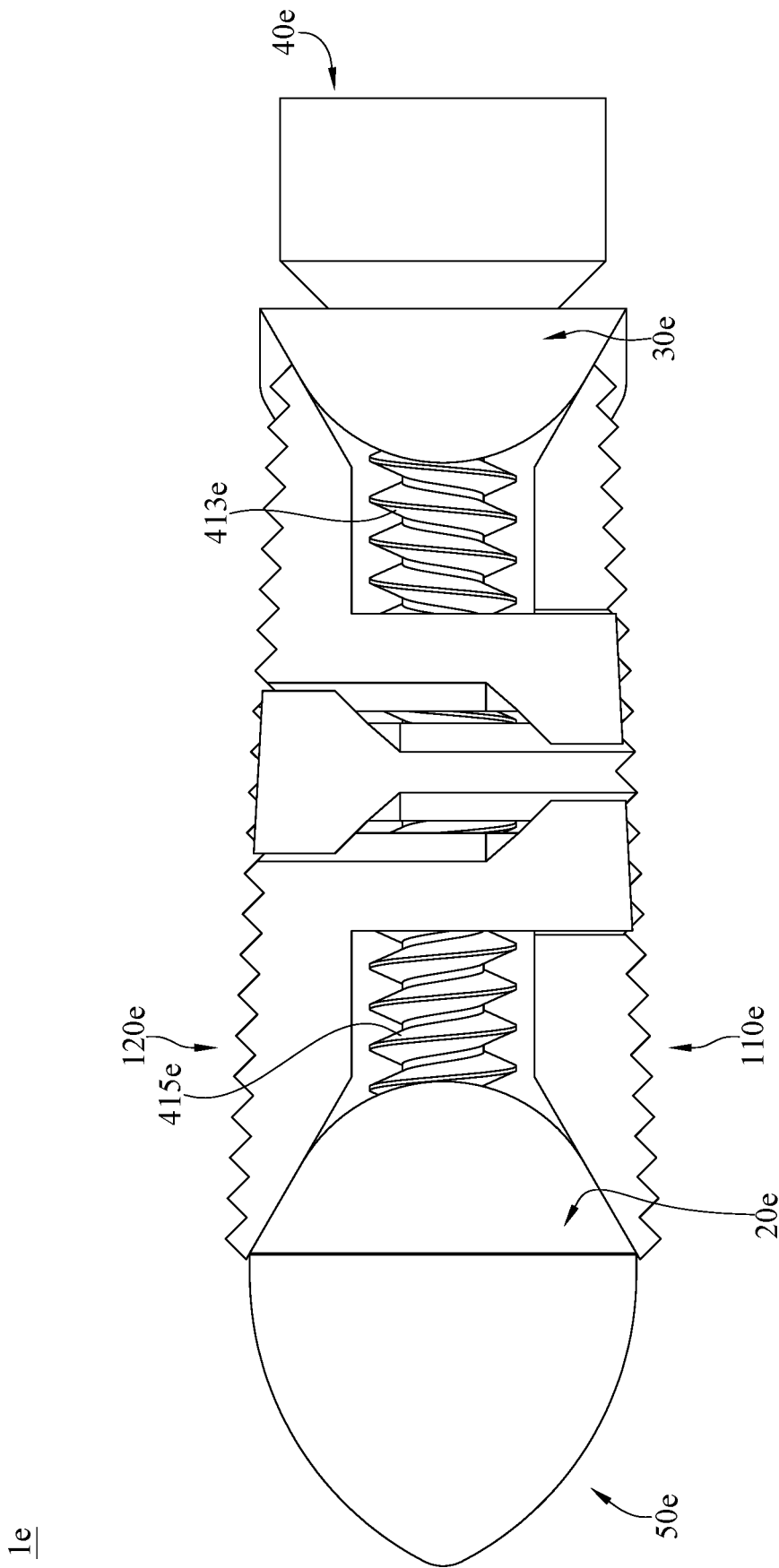
FIG. 11 depicts a side view of a spinal intervertebral body fusion device according to further another embodiment of the disclosure before the spinal intervertebral body fusion device is expanded.
Figure 12:
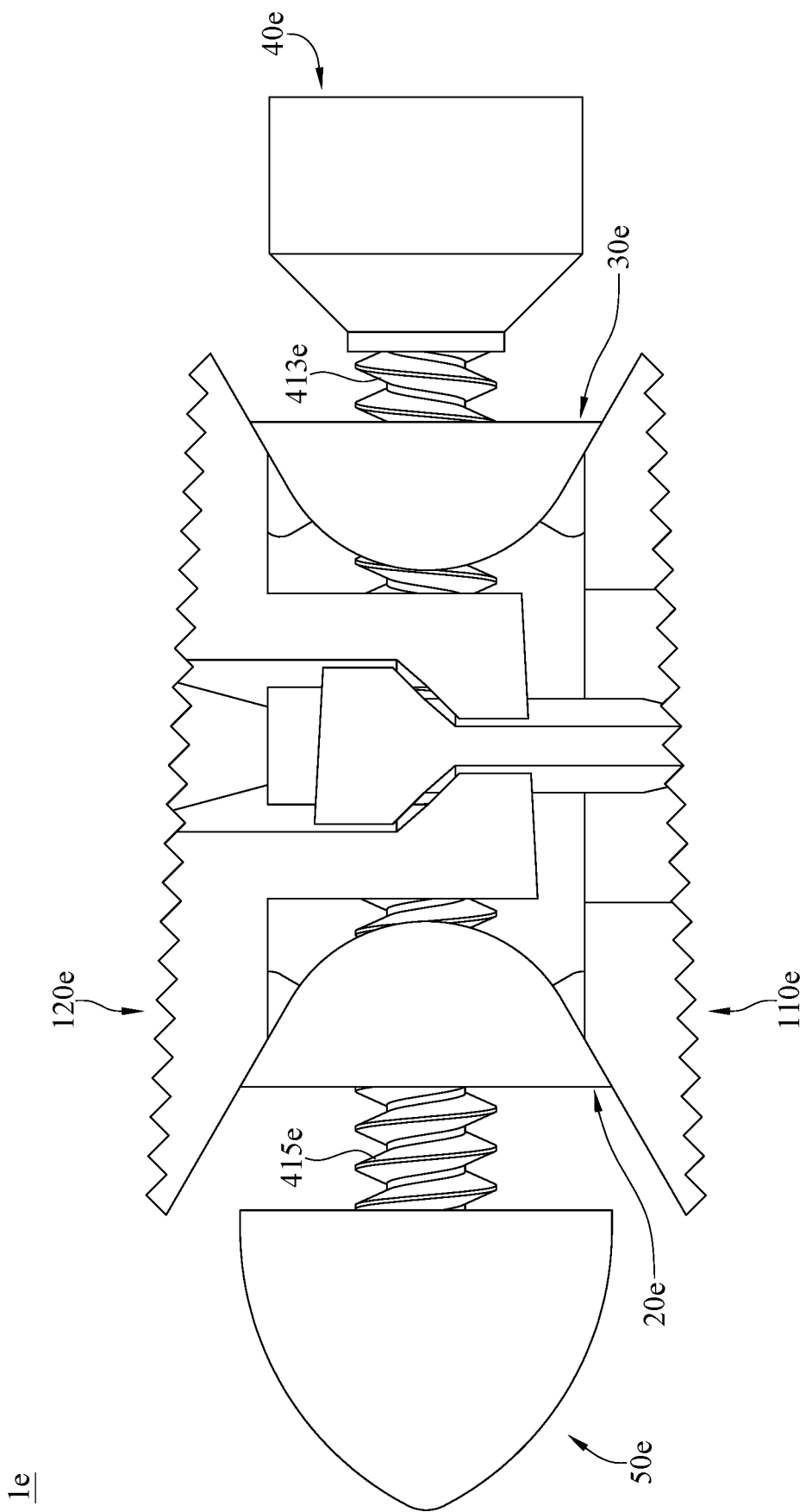
FIG. 12 depicts a side view of the spinal intervertebral body fusion device in FIG. 11 when the spinal intervertebral body fusion device is expanded.

In addition, the first pushing piece and the second pushing piece may not move toward or away from each other during the movement of the operative piece. Please refer to FIGS. 11-12, FIG. 11 depicts a side view of a spinal intervertebral body fusion device $1e$ according to further another embodiment of the disclosure before the spinal intervertebral body fusion device is expanded, and FIG. 12 depicts a side view of the spinal intervertebral body fusion device $1e$ in FIG. 11 when the spinal intervertebral body fusion device is expanded. For the purpose of simple description, only the differences between this and the previous embodiments will be illustrated below, and the same and similar parts can be obtained with the reference of the aforementioned discussions.

As shown, a first pushing piece $20e$ and a leading end $50e$ may be two independent objects, and the second pushing piece $30e$, in this embodiment, is allowed to be moved along an operative piece $40e$. In detail, the first pushing piece $20e$ is sleeved on and engaged with a threaded portion $415e$ of the operative piece $40e$, and one end of the threaded portion $415e$ is fixed to the leading end $50e$. As such, the first pushing piece $20e$ is movable along the threaded portion $415e$ of the operative piece $40e$ and able to move toward or away from the leading end $50e$. A neck portion $413e$ of the operative piece $40e$ also has threads (not numbered). The second pushing piece $30e$ is sleeved on and engaged with the threads of the neck portion $413e$. As such, the second pushing piece $30e$ is movable along the neck portion $413e$ and able to move toward or away from the first pushing piece 20e. When the operative piece 40e is forced to rotate, the first pushing piece 20e and the second pushing piece 30e clamp the front side and back side of the first supporting body 110e and the second supporting body 120e, such that the operative piece 40e is able to gradually pull the first pushing piece 20e towards the second pushing piece 30e and pull the second pushing piece 30e towards the first pushing piece 20e, achieving the adjustment of the distance between the first supporting body 110e and the second supporting body 120e. Since the operation of the operative piece 40e can simultaneously force the first pushing piece 20e and the second pushing piece 30e to move toward or away from each other, the distance between the end of the operative piece 40e and the tip of the leading end 50e does not change during status switching of the spinal intervertebral body fusion device 1e.

Figure 13:
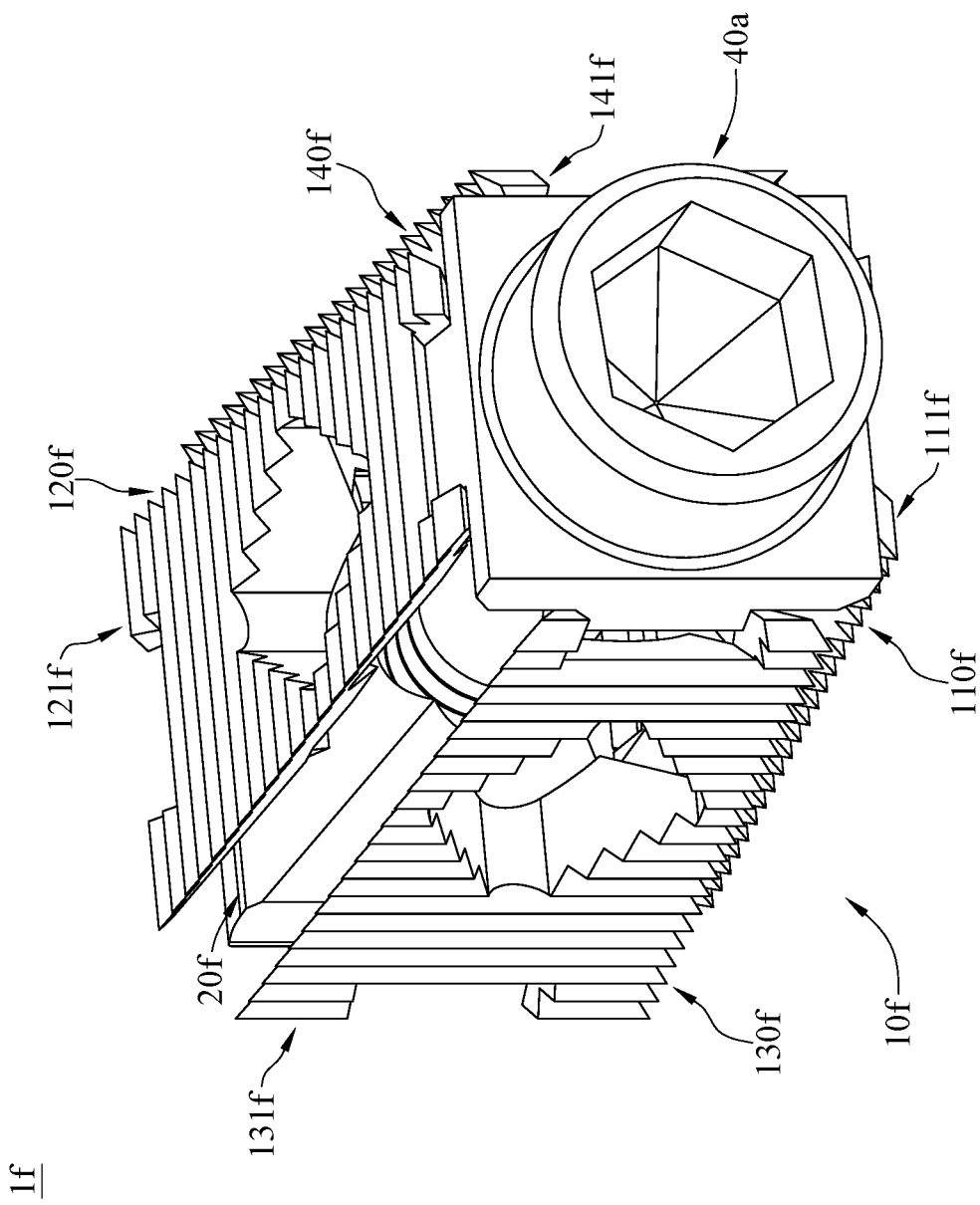
FIG. 13 is a perspective view of a spinal intervertebral body fusion device according to still further another embodiment of the disclosure.
Figure 14:
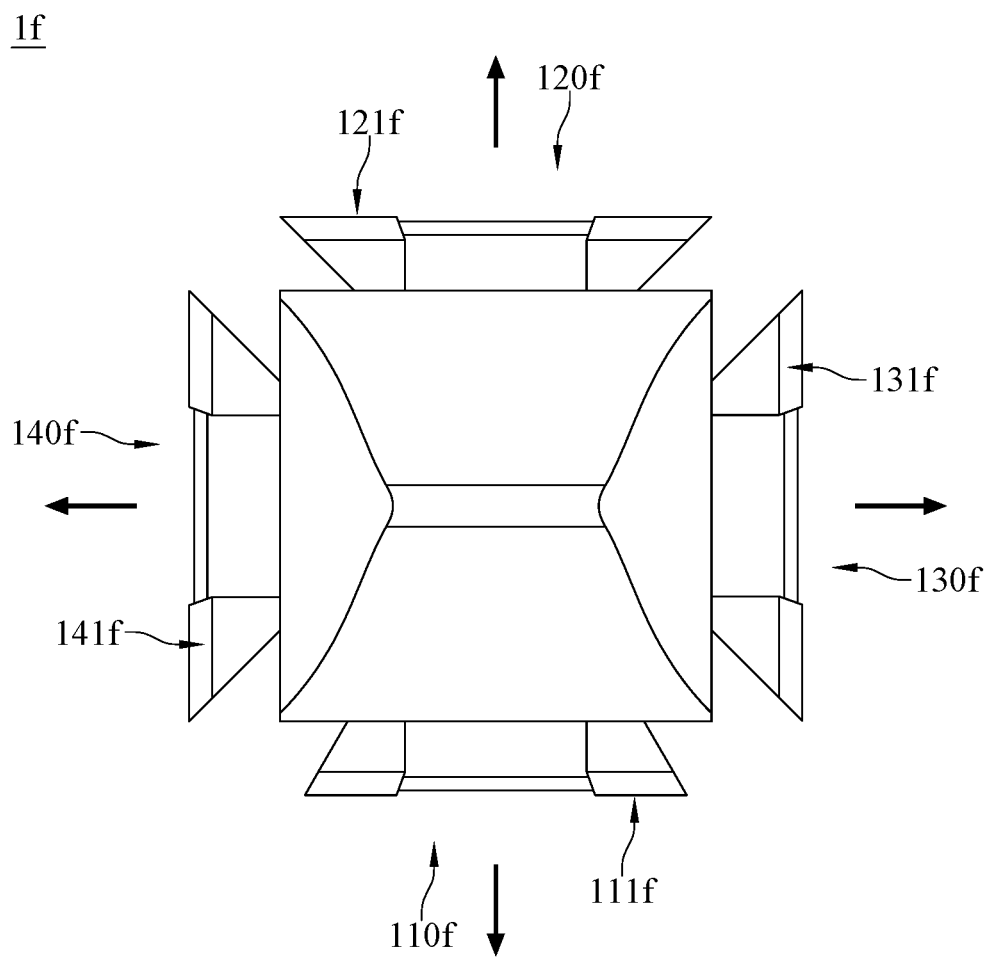
FIG. 14 is a front view of the spinal intervertebral body fusion device in FIG. 13.

Note that the adjustable spacer is not restricted to have two movable pieces. For example, please refer to FIGS. 13-14, FIG. 13 is a perspective view of a spinal intervertebral body fusion device if according to still further another embodiment of the disclosure, and FIG. 14 is a front view of the spinal intervertebral body fusion device if in FIG. 13. For the purpose of simple description, only the differences between this and the previous embodiments will be illustrated below, and the same and similar parts can be obtained with the reference of the aforementioned discussions.

As shown in FIG. 13, an adjustable spacer 10f of the spinal intervertebral body fusion device if includes a first supporting body 110f, a second supporting body 120f, a third supporting body 130f, and a fourth supporting body 140f which are respectively located at the four different sides thereof. That is, the first supporting body 110f, the second supporting body 120f, the third supporting body 130f, and the fourth supporting body 140f are respectively located at four different sides of an operative piece 40f of the spinal intervertebral body fusion device 1f. The movement of the operative piece 40f can force a first supporting plate portion 111f of the first supporting body 110f, a second supporting plate portion 121f of the second supporting body 120f, a third supporting plate portion 131f of the third supporting body 130f, and a fourth supporting plate portion 141f of the fourth supporting body 140f to move away from one another, such that the spinal intervertebral body fusion device if is adjustable in four different directions.

Specifically, the first supporting body 110f, the second supporting body 120f, the third supporting body 130f, and the fourth supporting body 140f are similar to the first supporting body and the second supporting body of the previous embodiments, and their features for installation may be misaligned to avoid structural interference, thus the same and similar parts will not be repeated hereinafter. In addition, based on the configuration of the adjustable spacer 10f, the first push surface 201f of the first pushing piece 20f and the second push surface 301f of the second pushing piece 30f may each include four surfaces or be a single conical surface corresponding to the inclined contact surfaces of the first supporting plate portion 111f, the second supporting plate portion 121f, the third supporting plate portion 131f, and the fourth supporting plate portion 141f. As such, the first pushing piece 20f and the second pushing piece 30f are able to simultaneously push the first supporting plate portion 111f, the second supporting plate portion 121f, the third supporting plate portion 131f, and the fourth supporting plate portion 141f while being forced by the operative piece 10f.

As the arrows shown in FIG. 14, when the adjustable spacer 10f is moved, the first supporting plate portion 111f, the second supporting plate portion 121f, the third supporting plate portion 131f, and the fourth supporting plate portion 141f are respectively moved toward four different directions. In some applications, during the process that the spinal intervertebral body fusion device if is switched from the unexpanded status to the expanded status, the distance between two opposite surfaces of the third supporting plate portion 131f and the fourth supporting plate portion 141f may increase from approximately 9.5 millimeters to 15 millimeters, and the distance between two opposite surfaces of the first supporting plate portion 111f and the second supporting plate portion 121f may increase from approximately 5 millimeters to 16 millimeters, but the disclosure is not limited thereto.

It is understood that the concept of the spinal intervertebral body fusion device 1a and the spinal intervertebral body fusion device 1b may apply to the spinal intervertebral body fusion device 1f. For example, in some embodiments, the first supporting body, the second supporting body, the third supporting body, and the fourth supporting body may have the thickness variation as the first supporting body and the second supporting body of the spinal intervertebral body fusion device 1a and/or the spinal intervertebral body fusion device 1b according to actual requirements.

According to the spinal intervertebral body fusion device as discussed in the above embodiments of the disclosure, the first supporting plate portion and the second supporting plate portion are movably installed to each other and together clamp the first pushing piece and the second pushing piece respectively at the first opening and the second opening on opposite sides, thus the operative piece that is located between the first supporting plate portion and the second supporting plate portion and connected to the first pushing piece and the second pushing piece is able to force the first pushing piece and the second pushing piece to clamp the first supporting plate portion and the second supporting plate portion so as to force the first supporting plate portion and the second supporting plate portion to move away from each other, achieving the size adjustment of the spinal intervertebral body fusion device. As such, the spinal intervertebral body fusion device is able to be adjusted to an optimal size to restore and maintain the height of the intervertebral space and position of the vertebral body.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A spinal intervertebral body fusion device, comprising:
an adjustable spacer, comprising a first supporting plate portion and a second supporting plate portion, wherein the first supporting plate portion is movably installed on the second supporting plate portion, the first supporting plate portion and the second supporting plate portion together form a first opening and a second opening which are respectively located at two opposite sides of the adjustable spacer;
a first pushing piece, located at the first opening and partially located between and clamped by the first supporting plate portion and the second supporting plate portion;
a second pushing piece, located at the second opening and partially located between and clamped by the first supporting plate portion and the second supporting plate portion; and an operative piece, located between the first supporting plate portion and the second supporting plate portion, and the operative piece movably disposed through the second pushing piece and screwed to the first pushing piece, wherein when the operative piece is activated, the operative piece forces the second pushing piece and the first pushing piece to move towards or away from each other to change a relative position of the first supporting plate portion and the second supporting plate portion;

the second pushing piece is partially located in a circular slot of the operative piece so that the operative piece is rotatable about an axis of the operative piece relative to the second pushing piece, and the second pushing piece is not movable along the axis of the operative piece relative to the operative piece.

2. The spinal intervertebral body fusion device according to claim 1, wherein the operative piece is an integrally formed single piece, the second pushing piece is an integrally formed single piece.

3. The spinal intervertebral body fusion device according to claim 1, wherein the first opening and the second opening are tapered toward each other.

4. The spinal intervertebral body fusion device according to claim 1, wherein the adjustable spacer further comprises at least one first engagement arm portion and at least one second engagement arm portion, the at least one first engagement arm portion is integrally formed on the first supporting plate portion and extends toward the second supporting plate portion, the at least one second engagement arm portion is integrally formed on the second supporting plate portion and extends toward the first supporting plate portion, the at least one first engagement arm portion is partially embedded in the at least one second engagement arm portion and is movable along the at least one second engagement arm portion.

5. The spinal intervertebral body fusion device according to claim 4, wherein the at least one first engagement arm portion and the at least one second engagement arm portion both extend in a curved manner.

6. The spinal intervertebral body fusion device according to claim 4, wherein the first supporting plate portion has at least one first inclined stopping surface corresponding to the at least one second engagement arm portion, an end of the at least one second engagement arm portion is located between the second supporting plate portion and the at least one first inclined stopping surface, the second supporting plate portion has at least one second inclined stopping surface corresponding to the at least one first engagement arm portion, an end of the at least one first engagement arm portion is located between the first supporting plate portion and the at least one second inclined stopping surface.

7. The spinal intervertebral body fusion device according to claim 1, wherein the first pushing piece has at least one first protrusion, at least one of the first supporting plate portion and the second supporting plate portion has at least one recess, and the at least one first protrusion is located in the at least one recess.

8. The spinal intervertebral body fusion device according to claim 1, wherein the second pushing piece has at least one second protrusion, at least one of the first supporting plate portion and the second supporting plate portion has at least one recess, and the at least one second protrusion is located in the at least one recess.

9. The spinal intervertebral body fusion device according to claim 1, wherein the operative piece is an integrally formed single piece, the operative piece comprises a head portion, a neck portion, and a threaded portion, the head portion is located at the second opening and partially clamped by the first supporting plate portion and the second supporting plate portion, the neck portion is located between the first supporting plate portion and the second supporting plate portion and connected between the head portion and the threaded portion, the head portion and the neck portion form the circular slot, at least part of the head portion and at least part of the neck portion are disposed through the second pushing piece, the neck portion has pores, and the threaded portion is screwed to the first pushing piece.

10. The spinal intervertebral body fusion device according to claim 1, wherein thicknesses of the first supporting plate portion and the second supporting plate portion decrease from the first opening towards the second opening.

11. The spinal intervertebral body fusion device according to claim 1, wherein thicknesses of the first supporting plate portion and the second supporting plate portion increase from the first opening towards the second opening.

12. The spinal intervertebral body fusion device according to claim 1, wherein the adjustable spacer further comprises a third supporting plate portion and a fourth supporting plate portion, the third supporting plate portion is movably installed on the fourth supporting plate portion, the first supporting plate portion, the second supporting plate portion, the third supporting plate portion, and the fourth supporting plate portion together form the first opening and the second opening and respectively located at different sides of the operative piece, the first pushing piece is partially located between and clamped by the first supporting plate portion, the second supporting plate portion, the third supporting plate portion, and the fourth supporting plate portion, the second pushing piece is partially located between and clamped by the first supporting plate portion, the second supporting plate portion, the third supporting plate portion, and the fourth supporting plate portion.

13. The spinal intervertebral body fusion device according to claim 1, wherein the operative piece and the second pushing piece were 3D printed together.

14. The spinal intervertebral body fusion device according to claim 1, wherein the first supporting plate portion and the second supporting plate portion were 3D printed together.

15. The spinal intervertebral body fusion device according to claim 1, wherein the second pushing piece is partially located in the circular slot of the operative piece and engaged with a part of the operative piece absent of threads.

* * * * *